United States Patent
Yu et al.

(10) Patent No.: US 10,467,497 B2
(45) Date of Patent: Nov. 5, 2019

(54) SYSTEM AND METHOD FOR PROVIDING ASSISTANCE IN SURGERY IN PRESENCE OF TISSUE DEFORMATION

(71) Applicant: SONY CORPORATION, Tokyo (JP)

(72) Inventors: Liangyin Yu, Fremont, CA (US); Bi Song, San Jose, CA (US); Ming-Chang Liu, San Jose, CA (US)

(73) Assignee: SONY CORPORATION, Tokyo (JP)

( * ) Notice: Subject to any disclaimer, the term of this patent is extended or adjusted under 35 U.S.C. 154(b) by 50 days.

(21) Appl. No.: 15/049,870

(22) Filed: Feb. 22, 2016

(65) Prior Publication Data

US 2017/0243344 A1 Aug. 24, 2017

(51) Int. Cl.
*G06K 9/62* (2006.01)
*A61B 5/055* (2006.01)
(Continued)

(52) U.S. Cl.
CPC .......... *G06K 9/6201* (2013.01); *A61B 5/0042* (2013.01); *A61B 5/0044* (2013.01); *A61B 5/055* (2013.01); *A61B 8/0808* (2013.01); *A61B 90/37* (2016.02); *G06F 17/50* (2013.01); *G06T 3/0081* (2013.01); *G06T 7/0012* (2013.01);
(Continued)

(58) Field of Classification Search
CPC ............................ G06T 7/0012; A61B 8/0808
See application file for complete search history.

(56) References Cited

U.S. PATENT DOCUMENTS

| 8,358,818 B2 | 1/2013 | Miga et al. | |
|---|---|---|---|
| 2008/0170791 A1* | 7/2008 | Eskildsen | G06K 9/48 382/199 |

(Continued)

FOREIGN PATENT DOCUMENTS

| EP | 2594200 A | 5/2013 |
|---|---|---|
| WO | 2013/116694 A1 | 8/2013 |

OTHER PUBLICATIONS

Warfield et al., "Real-Time Biomechanical Simulation of Volumetric Brain Deformation for Image Guided Neurosurgery", Proceedings of the 2000 ACM/IEEE Conference on Supercomputing, Npv. 4-10, 2000, pp. 1-16 (Year: 2006).*

(Continued)

*Primary Examiner* — Nay A Maung
*Assistant Examiner* — Jose Torres
(74) *Attorney, Agent, or Firm* — Chip Law Group

(57) ABSTRACT

Various aspects of a system and a method to provide assistance in a surgery in presence of tissue deformation are disclosed herein. In accordance with an embodiment, the system includes an electronic device that receives one or more tissue material properties of a plurality of surface structures of an anatomical portion. One or more boundary conditions associated with the anatomical portion may also be received. Surface displacement of the anatomical portion may be determined by matching a first surface of the anatomical portion before deformation with a corresponding second surface of the anatomical portion after the deformation. The volume displacement field of the anatomical portion may be computed based on the determined surface displacement, the received one or more tissue material properties, and the received one or more boundary conditions.

23 Claims, 8 Drawing Sheets

(51) Int. Cl.
*A61B 5/00* (2006.01)
*A61B 90/00* (2016.01)
*G06T 7/33* (2017.01)
*G06T 3/00* (2006.01)
*G06F 17/50* (2006.01)
*A61B 8/08* (2006.01)
*G06T 7/00* (2017.01)

(52) U.S. Cl.
CPC .............. *G06T 7/33* (2017.01); *A61B 5/0077* (2013.01); *A61B 2090/374* (2016.02); *A61B 2090/3762* (2016.02); *A61B 2505/05* (2013.01); *A61B 2576/026* (2013.01); *G06T 2207/10012* (2013.01); *G06T 2207/10028* (2013.01); *G06T 2207/10088* (2013.01); *G06T 2207/30016* (2013.01)

(56) References Cited

U.S. PATENT DOCUMENTS

| | | | |
|---|---|---|---|
| 2009/0310835 A1* | 12/2009 | Kaus | G06T 17/20 382/128 |
| 2011/0176746 A1* | 7/2011 | Bucki | G06T 7/30 382/293 |
| 2012/0330635 A1 | 12/2012 | Miga et al. | |
| 2013/0279784 A1 | 10/2013 | Gill et al. | |
| 2014/0003698 A1 | 1/2014 | Ruijters et al. | |
| 2014/0161338 A1 | 6/2014 | Machado | |
| 2014/0226884 A1* | 8/2014 | Porikli | A61N 5/1037 382/131 |
| 2014/0294271 A1* | 10/2014 | Madabhushi | G06T 7/0014 382/131 |
| 2014/0369584 A1* | 12/2014 | Fan | A61B 6/501 382/131 |
| 2016/0027178 A1* | 1/2016 | Yu | A61B 5/055 600/407 |

OTHER PUBLICATIONS

International Search Report and Written Opinion of PCT Application No. PCT/US17/15439, dated Apr. 7, 2017, 11 pages.
P. Hastreiter et al, "Registration Techniques for the Analysis of the Brain Shift in Neurosurgery", Computers & Graphics, Jun. 2000, pp. 385-389, vol. 24, Issue No. 3.
Grzegorz Soza et al, "Non-Linear Intraoperative Correction of Brain Shift With 1.5 T Data", Computer Graphics Group, 2003, pp. 5.
Extended European Search Report of EP Patent Application No. 17756962.1, dated Jul. 16, 2019, 09 pages.
Sun, et al., "Near Real-Time Computer Assisted Surgery for Brain Shift Correction Using Biomechanical Models", IEEE Journal of Translational Engineering in Health and Medicine, vol. 2, May 30, 2014, 13 pages.
Skrinjar, et al., "Steps Toward a Stereo-Camera-Guided Biomechanical Model for Brain Shift Compensation", IPMI '01 Proceedings of the 17th International Conference on Information Processing in Medical Imaging, Jun. 18-21, 2001, pp. 183-189.

* cited by examiner

SYSTEM AND METHOD FOR PROVIDING ASSISTANCE IN SURGERY IN PRESENCE OF TISSUE DEFORMATION

CROSS-REFERENCE TO RELATED APPLICATIONS/INCORPORATION BY REFERENCE

None.

FIELD

Various embodiments of the disclosure relate to a system and a method to provide assistance in a surgery. More specifically, various embodiments of the disclosure relate to a system and a method to provide assistance in a surgery in the presence of tissue deformation.

BACKGROUND

Advancements in the field of medical imaging techniques and associated sensors and/or devices have made possible, the ability to visualize the interior of a body for clinical analysis and medical purposes. In certain scenarios, a surgeon may plan a surgery to access complicated anatomical structures of a subject before the surgery is actually performed. The surgeon may also plan one or more paths to access a region-of-interest of an anatomical portion under surgery. Due to the complexity of the anatomical structures, and certain deformation of tissue after exposure of the tissue of the anatomical portion during the surgery, it may be difficult to mentally evaluate the displacement of the anatomical structures during the surgery. Unless compensated suitably, it may be difficult to perform the surgery accurately and safely.

Current systems and technologies that use intraoperative imaging of the anatomical portion to visualize the anatomical structures and the deformation of tissues of the anatomical portion that is exposed during the surgery. However, such intraoperative imaging may be unsafe for the subject for various reasons, such as a risk of exposure to radiation during the intraoperative imaging. Thus, an improved technique and/or system may be required that reduces complexities for the surgeon, and provides safe, accurate, and quick assistance to perform surgery with improved accuracy and safety.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

A system and a method are described to provide assistance in a surgery in presence of tissue deformation as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
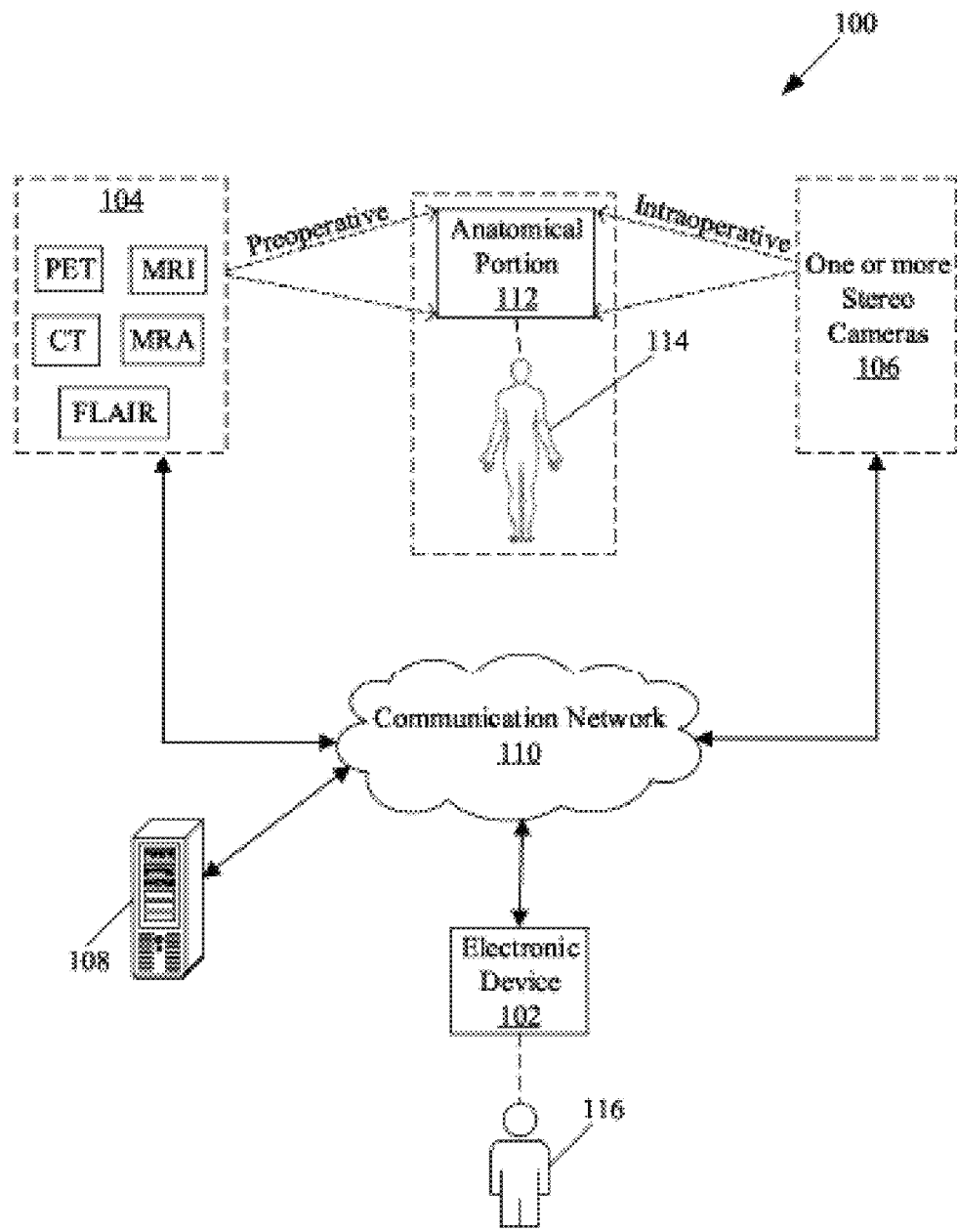
FIG. 1 is a block diagram that illustrates a network environment to provide assistance in a surgery in presence of tissue deformation, in accordance with an embodiment of the disclosure.

The following described implementations may be found in the disclosed system and method to provide assistance in a surgery in presence of tissue deformation. Exemplary aspects of the disclosure may include receipt of one or more tissue material properties of a plurality of surface structures of an anatomical portion by an electronic device. One or more boundary conditions associated with the anatomical portion may also be received. Surface displacement of the anatomical portion may be determined from a match between a first surface of the anatomical portion before deformation with a corresponding second surface of the anatomical portion after the deformation. The volume displacement field of the anatomical portion may be computed based on the determined surface displacement, the received one or more tissue material properties, and/or the received one or more boundary conditions.

In accordance with an embodiment, the plurality of surface structures of the anatomical portion may correspond to heterogeneous anatomical surface structures. In accordance with an embodiment, the anatomical portion may correspond to at least a portion of a brain. When present in the anatomical portion of a subject, the plurality of surface structures may correspond to the cortex, blood vessels, ventricles, and/or a tumor structure when present in the anatomical portion of a subject.

In accordance with an embodiment, the received one or more boundary conditions may include a displaced boundary condition and/or a stationary boundary condition. The plurality of surface structures of the anatomical portion may be reconstructed based on registration of a dataset associated with the anatomical portion. The dataset may be received from a magnetic resonance imaging (MRI) scanner or from multimodal sources that may include the MRI scanner.

In accordance with an embodiment, surface segmentation may be performed for the plurality of surface structures of the anatomical portion. The surface segmentation may be performed by use of MRI data before the deformation when the anatomical portion is in an unopened state prior to a surgery. In accordance with an embodiment, a three-dimensional (3D) structure of the anatomical portion may be created based on a two-dimensional (2D) to 3D geometry processing and the surface segmentation. The created 3D structure may include the plurality of surface structures that correspond to the first surface.

In accordance with an embodiment, stereo vision may be utilized to reconstruct one or more surfaces of the anatomical portion after deformation. The stereo vision may be utilized for the determination of the surface displacement after deformation when the anatomical portion is in an opened state during surgery. The reconstructed one or more surfaces of the anatomical portion after deformation may correspond to the second surface.

In accordance with an embodiment, a registration may be performed of the reconstructed one or more surfaces of the anatomical portion in the opened state to the 3D structure of the anatomical portion in the unopened state in a 3D coordinate system. In instances when the anatomical portion is at least a portion of the brain of the subject, the registration may be performed by use of an alignment of bone structures of the skull of the subject.

In accordance with an embodiment, displacement of voxels associated with the deformation of the anatomical portion may be measured in a finite element method (FEM) framework. The displacement of voxels may be measured based on current position of the displaced voxels after the deformation with respect to the then position of the corresponding voxels before the deformation. The measurement may be performed within the volume of the anatomical portion and may be based on the determined surface displacement. The measurement of the displacement of voxels may correspond to the computation of the volume displacement field. The volume of the anatomical portion may represent the entire tissue content of the anatomical portion.

In accordance with an embodiment, the computed volume displacement field may be applied for deformation compensation to one or more of the plurality of surface structures. A plurality of multi-dimensional graphical views of the anatomical portion may be generated. The plurality of multi-dimensional graphical views may be generated after the deformation. Such graphical views may be used to assist during the surgery when the anatomical portion is deformed in the opened state. The generated plurality of multi-dimensional graphical views may include the displaced one or more regions-of-interest in the plurality of surface structures of the anatomical portion. The generated plurality of multi-dimensional graphical views may further include volume displacement within the anatomical portion that represents a change in volume after the deformation. The plurality of multi-dimensional graphical views may correspond to a 3D view of the anatomical portion that includes the plurality of surface structures from one or more perspectives.

FIG. 1 is a block diagram that illustrates a network environment to provide assistance in a surgery in presence of tissue deformation, in accordance with an embodiment of the disclosure. With reference to FIG. 1, there is shown a network environment 100 that may include an electronic device 102, a plurality of medical imaging devices 104, one or more stereo cameras 106, a server 108, and a communication network 110. There is further shown an anatomical portion 112, and one or more users, such as a human subject 114 and a surgeon 116. The electronic device 102 may be communicatively coupled to the plurality of medical imaging devices 104, the one or more stereo cameras 106, and the server 108, via the communication network 110.

The electronic device 102 may comprise suitable logic, circuitry, interfaces, and/or code that may be configured to determine surface displacement of the anatomical portion 112. The surface displacement may be determined by matching surfaces of the anatomical portion 112 before and after deformation. The electronic device 102 may provide a real-time or near real-time assistance in a surgery in the presence of the deformation of tissue of the anatomical portion 112 that is subjected to the surgery. Examples of the electronic device 102 may include, but are not limited to, a user terminal associated with a computer-assisted surgical system or a robot-assisted surgical system, a medical device, an electronic surgical instrument, a display device, and/or a computing device.

The plurality of medical imaging devices 104 may correspond to diagnostic equipment used to create visual representations of internal structures or anatomical portions, such as the anatomical portion 112, of the human subject 114. Such visual representations of the internal structures or the anatomical portions may be created for clinical analysis and medical intervention when the human subject 114 is in a preoperative state. The plurality of medical imaging devices 104 may be multimodal sources used to obtain datasets related to the anatomical portion 112. Examples of the plurality of medical imaging devices 104 may include, but are not limited to, an X-ray computed tomography (CT) scanner, a magnetic resonance imaging (MRI) scanner, a magnetic resonance angiography (MRA) scanner, a fluid-attenuated inversion recovery (FLAIR) based scanner, and/or a positron emission tomography (PET) scanner.

The one or more stereo cameras 106 may comprise suitable logic, circuitry, interfaces, and/or code that may be configured to capture and generate 3D stereoscopic images or 3D-structure data for an anatomical portion, such as the anatomical portion 112, of the human subject 114. A plurality of images may be acquired from different viewpoints in space to generate the 3D stereoscopic images or 3D-structure data of the anatomical portion 112 in an intraoperative state. The plurality of images, such as stereo image pairs, may be acquired by use of multiple cameras from different viewpoints, multiple camera lenses of a single stereo camera, or a single moving camera. The 3D-structure data of an exposed surface, such as exposed brain surface in intraoperative state, may be reconstructed from the stereo vision of the one or more stereo cameras 106. In accordance with an embodiment, the one or more stereo cameras 106 may be mounted on a surgical microscope used to perform microsurgery.

The server 108 may comprise suitable logic, circuitry, interfaces, and/or code that may be configured to receive and centrally store one or more datasets obtained from the plurality of medical imaging devices 104. The one or more datasets may correspond to the imaging data of the anatomical portion 112 in the preoperative state before occurrence of tissue deformation in the anatomical portion 112. In accordance with an embodiment, the one or more datasets may correspond to multimodal images. In accordance with an embodiment, the server 108 may be configured to provide the pre-stored one or more datasets to the electronic device 102, via the communication network 110. In accordance with an embodiment, the electronic device 102 may directly receive the one or more datasets from the plurality of medical imaging devices 104. In accordance with an embodiment, both the server 108 and the electronic device 102 may be part of a computer-assisted surgical system. In accordance with an embodiment, the server 108 may be implemented as a plurality of cloud-based resources by use of several technologies that are well known to those skilled in the art. Examples of the server 108 may include, but are not limited to, a database server, a file server, an application server, a web server, and/or their combination.

The communication network 110 may include a medium through which the electronic device 102, the plurality of medical imaging devices 104, the one or more stereo cameras 106, and/or the server 108 may communicate with each other. The communication network 110 may be a wired or wireless communication network. Examples of the communication network 110 may include, but are not limited to, a Local Area Network (LAN), a Wireless Local Area Network (WLAN), a cloud network, a Long Term Evolution (LTE) network, a plain old telephone service (POTS), a Metropolitan Area Network (MAN), and/or the Internet. Various devices in the network environment 100 may be configured to connect to the communication network 110, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, cellular communication protocols, and/or Bluetooth (BT) communication protocols.

The anatomical portion 112 may be an anatomical region and/or an organ of a subject, such as the human subject 114. The anatomical portion 112 may include a plurality of surface structures. The plurality of surface structures of the anatomical portion 112 may be heterogeneous anatomical surface structures. Each surface structure of the plurality of surface structures of the anatomical portion 112 may have its own tissue material properties. In accordance with an embodiment, the anatomical portion 112 may be a brain (cranial region), or at least a portion of a brain of the human subject 114. In such an embodiment, the plurality of surface structures may be the cortex, blood vessels, and/or ventricles of the brain. The plurality of surface structures may further include a tumor structure within the brain of the human subject 114. In accordance with an embodiment, the anatomical portion 112 may be a heart (cardiac region), which also includes heterogeneous anatomical surface structures.

A person with ordinary skill in the art will understand that the scope of the disclosure is not limited to implementation of the disclosed system and method to assist in a surgery of the anatomical portion 112 of the human subject 114, as shown. In accordance with an embodiment, the disclosed system and method may be used to assist in a surgery of anatomical portions or anatomical regions of an animal subject. Further, the disclosed system and method may also be useful to provide assistance in a surgery of anatomical portions or regions other than the brain or the heart, as discussed above.

In operation, the electronic device 102 may be configured to receive at least a dataset associated with the anatomical portion 112 from the MRI scanner. The dataset may include a plurality of 2D images that represents slice planes taken through a volume of the anatomical portion 112, such as slices through the skull of the human subject 114. The dataset may correspond to MRI data taken prior to a surgery (preoperative state). The electronic device 102 may be configured to register the received dataset associated with the anatomical portion 112.

In accordance with an embodiment, the electronic device 102 may be configured to receive a plurality of datasets associated with the anatomical portion 112 from multimodal sources. The multimodal sources may be the plurality of medical imaging devices 104 that employ the MRI-, the CT-, the PET-, the FLAIR-, and the MRA-based medical imaging techniques to acquire the plurality of datasets associated with the anatomical portion 112. In accordance with an embodiment, to register the plurality of datasets associated with the anatomical portion 112 from different multimodal sources, such as the CT and the MRI, the plurality of datasets must have overlapped content. In such an embodiment, the electronic device 102 may be configured to register the received plurality of datasets associated with the anatomical portion 112, based on identification of the overlapped content.

Based on the received dataset from the MRI scanner or the plurality of dataset from the multimodal sources, the electronic device 102 may be configured to reconstruct a plurality of surface structures of the anatomical portion 112, based on the registration. For example, when the anatomical portion 112 is the brain, the electronic device 102 may reconstruct brain surface structures, such as cerebellum cortex, cerebrum cortex, brain vessels structure, and/or ventricles.

In accordance with an embodiment, the electronic device 102 may be configured to perform surface segmentation for the reconstructed plurality of surface structures of the anatomical portion 112. The surface segmentation may be performed by use of the MRI data before the deformation of tissue of the anatomical portion 112, when the anatomical portion 112 is in an unopened state prior to the surgery.

In accordance with an embodiment, the electronic device 102 may be configured to create a 3D structure of the anatomical portion 112, based on a 2D-to-3D geometry processing and the surface segmentation. The 2D-to-3D geometry processing may be a mesh geometry processing or a grid geometry processing. The created 3D structure may include the reconstructed plurality of surface structures. The electronic device 102 may be configured to display one or more views of the created 3D structure of the anatomical portion 112. Such displayed one or more views may correspond to the 3D structure of the anatomical portion 112 before the deformation of tissue of the anatomical portion 112 prior to the surgery. The surgeon 116 may plan the surgery to be conducted for the anatomical portion 112, based on the displayed one or more views of the 3D structure of the anatomical portion 112.

In accordance with an embodiment, in the intraoperative state (when the surgery is performed), the tissue of the anatomical portion 112 may become deformed due to one or more factors. Examples of the one or more factors may include, but are not limited to, a level of complexity of the tissue structure of the anatomical portion 112, gravitational forces, and/or loss of a fluid, such as cerebrospinal fluid, around the anatomical portion 112 when the tissue is exposed in the intraoperative state. The one or more factors may include an extent of softness of the tissue of the anatomical portion 112, blood pressure, and/or an extent of displacement of a protective covering or a supportive structure associated with the anatomical portion 112 during the surgery. The deformation of the tissue of the anatomical portion 112 may displace certain anatomical tissue structures, and thereby the paths planned previously to access a region-of-interest in the anatomical portion 112 may also be changed during the surgery. Thus, it may be advantageous for the surgeon 116 to quickly and accurately know the regions of deformation and the displacement of the tissue structures while performing the surgery.

In accordance with an embodiment, the electronic device 102 may be configured to utilize stereo vision for the determination of the surface displacement after deformation when the anatomical portion 112 is in an opened state during the surgery. The one or more stereo cameras 106 may be used to capture and generate 3D stereoscopic images or 3D-structure data for the anatomical portion 112 in the intraoperative state. The electronic device 102 may be configured to reconstruct one or more surfaces of the anatomical portion 112 (after deformation).

In accordance with an embodiment, the electronic device 102 may be configured to perform a registration of the reconstructed one or more surfaces of the anatomical portion 112, in the opened state, to the 3D structure of the anatomical portion 112 in the unopened state in a 3D coordinate system. In accordance with an embodiment, the registration may be performed by use of a common reference point of the anatomical portion 112, which may be invariable in both phases of the surgery, such as the preoperative state before the tissue deformation and the intraoperative state after the tissue deformation. For example, when the anatomical portion 112 is the brain, an alignment of bone structure (a common and invariable reference point in this case) of a skull of human subject 114 may be used for the registration. Such registration may be a single-step registration.

In accordance with an embodiment, the electronic device 102 may be configured to receive one or more tissue material properties of the plurality of surface structures of the anatomical portion 112. The electronic device 102 may be configured to further receive one or more boundary conditions associated with the anatomical portion 112. In accordance with an embodiment, the electronic device 102 may be configured to receive two boundary conditions, such as a displaced (or deformation) boundary condition and a stationary boundary condition. For example, not all surface structures of the anatomical portion 112 may be displaced. Further, due to the positioning of the plurality of surface structures, some surface structures are more disposed to deformation as compared to other surface structures. The surface structures with a lower propensity to deform due to favorable positioning or support from associated anatomical structures may correspond to the stationary boundary condition. The surface structures that exhibit comparatively more propensity to deform, as described above, may correspond to the deformation boundary condition. Thus, such received boundary conditions associated with the anatomical portion 112 may increase the accuracy of the determination of the surface displacement of the anatomical portion 112.

In accordance with an embodiment, the electronic device 102 may be configured to match a first surface of the anatomical portion 112 (before deformation) with a corresponding second surface of the anatomical portion 112 (after the deformation). The first surface and the second surface may be the same surfaces of the anatomical portion 112, at different time points and/or the deformation states. The first surface of the anatomical portion 112 may correspond to at least one or more surfaces of the created 3D structure (before deformation), as described above. The second surface of the anatomical portion 112 may correspond to the reconstructed one or more surfaces of the anatomical portion 112 (after deformation). In accordance with an embodiment, the electronic device 102 may be configured to determine surface displacement of the anatomical portion 112, based on a result of the match.

In accordance with an embodiment, the received one or more tissue material properties of the plurality of surface structures, the received one or more boundary conditions, and the determined surface displacement of the anatomical portion 112 may be fed to a finite element method (FEM) framework. In accordance with an embodiment, the electronic device 102 may be configured to compute a volume displacement field of the anatomical portion 112. The computed volume displacement may be based on the determined surface displacement, the received one or more tissue material properties, and the received one or more boundary conditions. The electronic device 102 may be configured to utilize the FEM framework for such computation of the volume displacement field of the anatomical portion 112.

In accordance with an embodiment, the electronic device 102 may be configured to measure displacement of voxels associated with the anatomical portion 112 (after the deformation), with respect to the anatomical portion 112 (before the deformation) in the FEM framework. The measurement of displacement of voxels may be performed within an entire volume, such as the entire tissue content of the anatomical portion 112, based on the determined surface displacement. The measurement of the displacement of voxels may correspond to the computation of the volume displacement field.

In accordance with an embodiment, the electronic device 102 may be configured to apply the computed volume displacement field for deformation compensation to one or more of the plurality of surface structures of the anatomical portion 112. The electronic device 102 may then generate a plurality of multi-dimensional graphical views of the anatomical portion 112 (after the deformation). The generated plurality of multi-dimensional graphical views may include displaced one or more regions-of-interest in the plurality of surface structures of the anatomical portion 112 and/or volume displacement within the anatomical portion 112. The volume displacement may represent a change in volume after the deformation. The plurality of multi-dimensional graphical views may correspond to one or more perspectives of a 3D view of the anatomical portion 112, which includes the plurality of surface structures.

The electronic device 102 may be configured to control display of the generated plurality of multi-dimensional graphical views of the anatomical portion 112 (after the deformation). Such generation and display of the plurality of multi-dimensional graphical views of the anatomical portion 112 in the presence of the tissue deformation may occur to assist the surgeon 116 in real-time or near real-time while the surgeon 116 performs the surgery of the anatomical portion 112. The generated plurality of multi-dimensional graphical views may be user-controlled, modified, and visualized as per medical requirement.

Figure 2:
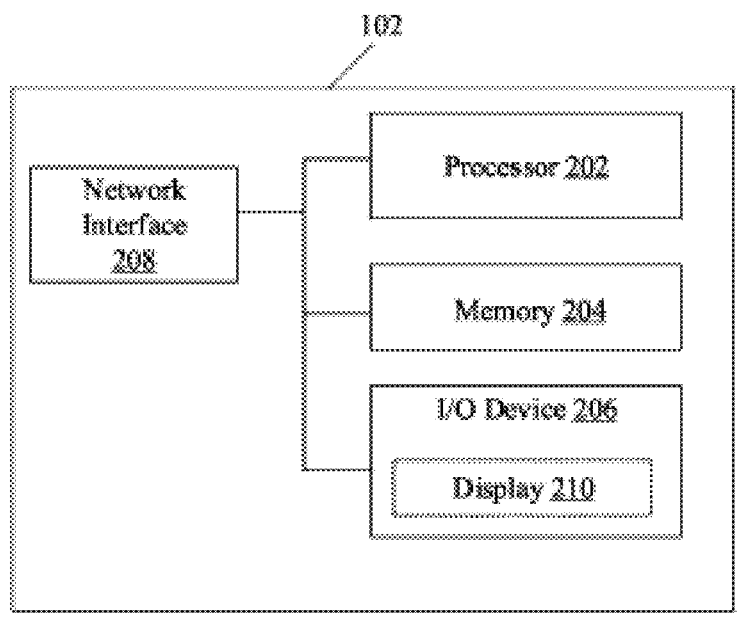
FIG. 2 illustrates a block diagram of an exemplary electronic device that provides assistance in a surgery in presence of tissue deformation, in accordance with an embodiment of the disclosure.

FIG. 2 illustrates a block diagram of an exemplary electronic device that provides assistance in a surgery in presence of tissue deformation, in accordance with an embodiment of the disclosure. FIG. 2 is explained in conjunction with elements from FIG. 1. With reference to FIG. 2, there is shown the electronic device 102. The electronic device 102 may comprise one or more processors, such as a processor 202, a memory 204, one or more input/output (I/O) devices, such as an I/O device 206, and a network interface 208. The I/O device 206 may include a display 210.

The processor 202 may be communicatively coupled to the memory 204, the I/O device 206, and the network interface 208. The network interface 208 may communicate with the plurality of medical imaging devices 104, the one or more stereo cameras 106, and/or one or more servers, such as the server 108, via the communication network 110 under the control of the processor 202.

The processor 202 may comprise suitable logic, circuitry, interfaces, and/or code that may be configured to execute a set of instructions stored in the memory 204. The processor 202 may be implemented based on a number of processor technologies known in the art. Examples of the processor 202 may be an X86-based processor, X86-64-based processor, a Reduced Instruction Set Computing (RISC) processor, an Application-Specific Integrated Circuit (ASIC) processor, a Complex Instruction Set Computing (CISC) processor, a central processing unit (CPU), an Explicitly Parallel Instruction Computing (EPIC) processor, a Very Long Instruction Word (VLIW) processor, and/or other processors or circuits.

The memory 204 may comprise suitable logic, circuitry, and/or interfaces that may be configured to store a machine code and/or a set of instructions executable by the processor 202. The memory 204 may be configured to store information from one or more user profiles associated with physiological data or medical history of the subject, such as the human subject 114. In accordance with an embodiment, the medical history of the subject, such as the human subject 114, may not be stored. Alternatively, the one or more user profile information items may be stored at the server 108. The memory 204 may store a user interface (UI), such as an application UI. The UI may be a three-dimensional (3D) viewer or a two-dimensional (2D) viewer used to view the plurality of multi-dimensional graphical views of the anatomical portion 112. The memory 204 may be further configured to store operating systems and associated applications. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may comprise suitable logic, circuitry, interfaces, and/or code that may be configured to receive an input from and provide an output to a user, such as the surgeon 116. The I/O device 206 may include various input and output devices that may be configured to facilitate a communication between the electronic device 102 and the user, such as the surgeon 116. Examples of the input devices may include, but are not limited to, a touch screen, a camera, a keyboard, a mouse, a joystick, a microphone, a motion sensor, a light sensor, and/or a docking station. Examples of the output devices may include, but are not limited to, the display 210, a projector screen, and/or a speaker.

The network interface 208 may comprise suitable logic, circuitry, interfaces, and/or code that may be configured to communicate with the plurality of medical imaging devices 104, the one or more stereo cameras 106, and/or the server 108, via the communication network 110 (as shown in FIG. 1). The network interface 208 may implement known technologies to support wired or wireless communication of the electronic device 102 with the communication network 110. The network interface 208 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer. The network interface 208 may communicate via wired or wireless communication with the communication network 110. The wireless communication may use one or more of the communication standards, protocols and technologies, such as Global System for Mobile Communications (GSM), Enhanced Data GSM Environment (EDGE), wideband code division multiple access (W-CDMA), code division multiple access (CDMA), time division multiple access (TDMA), Bluetooth, Long-Term Evolution (LTE), Wireless Fidelity (Wi-Fi) (such as IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

The display 210 may be realized through several known technologies, such as Cathode Ray Tube (CRT) based display, Liquid Crystal Display (LCD), Light Emitting Diode (LED) based display, Organic LED display technology, retina display technology, and/or the like. In accordance with an embodiment, the display 210 may be capable of receiving input from the user (such as the surgeon 116). In such a scenario, the display 210 may be a touch screen that enables the user to provide the input. The touch screen may correspond to at least one of a resistive touch screen, a capacitive touch screen, or a thermal touch screen. In accordance with an embodiment, the display 210 may receive input through a virtual keypad, a stylus, a gesture-based input, and/or a touch-based input. In such a case, the input device may be integrated within the display 210.

In operation, the processor 202 may be configured to receive at least one dataset associated with the anatomical portion 112 by use of the network interface 208. The at least one dataset may be received from the MRI scanner, via the communication network 110. The processor 202 may be further configured to communicate the received dataset to the processor 202 by use of the network interface 208. The processor 202 may be configured to register the received dataset associated with the anatomical portion 112. In accordance with an embodiment, the processor 202 may be configured to receive a plurality of datasets associated with the anatomical portion 112 from the multimodal sources, such as the plurality of medical imaging devices 104. The operations performed by the processor 202 have been further described in FIGS. 3A to 3D with an example of a brain of the human subject 114 as the anatomical portion 112 of interest. Notwithstanding, the anatomical portion 112 may also be other anatomical portions of the subject, without limiting the scope of the disclosure.

Figure 3A:
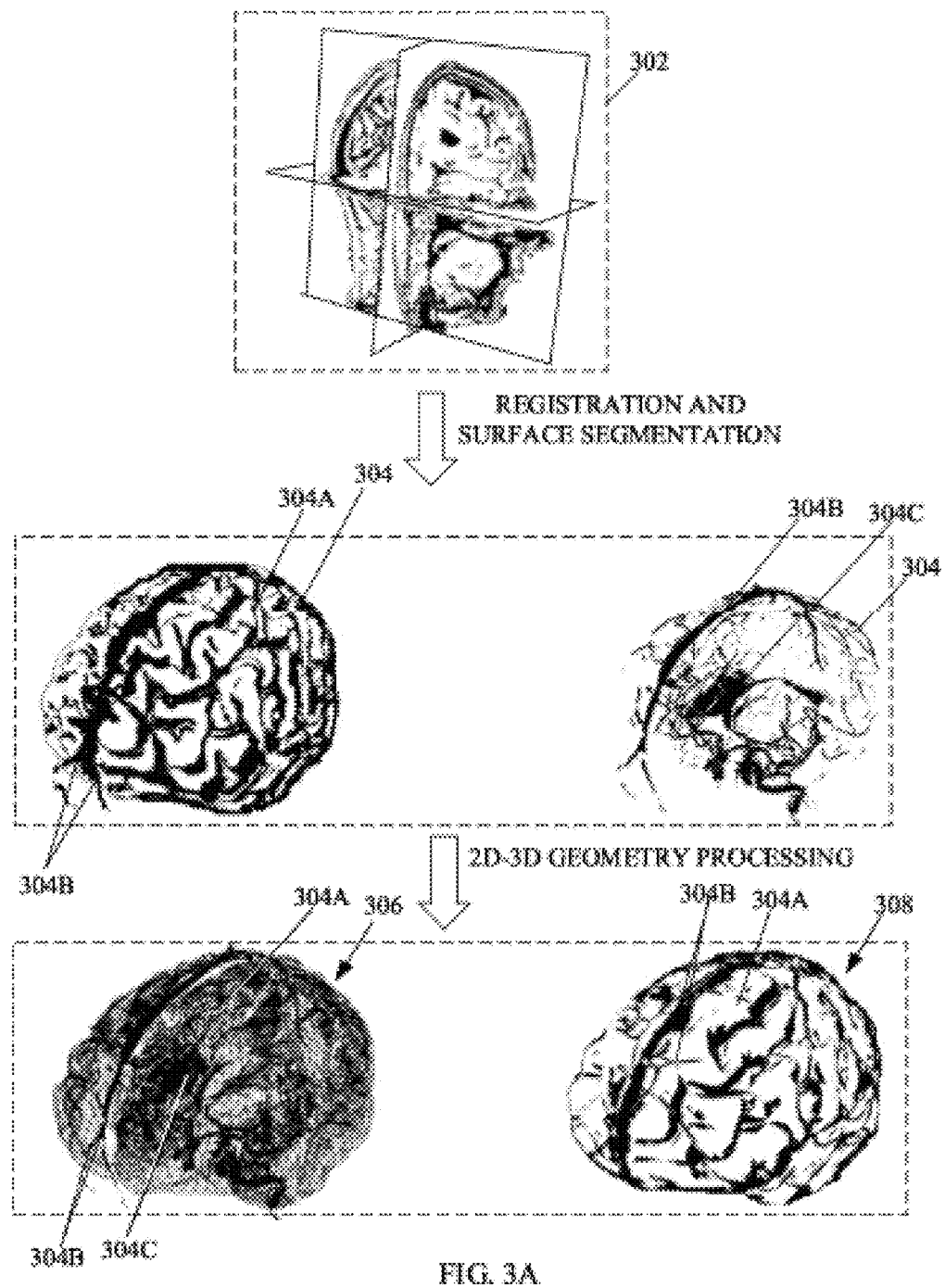
FIGS. 3A to 3D, collectively, illustrate an exemplary scenario for implementation of the system and method to provide assistance in a surgery in presence of tissue deformation, in accordance with an embodiment of the disclosure.

FIGS. 3A to 3D, collectively, illustrate an exemplary scenario for implementation of the system and method to provide assistance in a surgery in presence of tissue deformation, in accordance with an embodiment of the disclosure. FIG. 3A illustrates processing of MRI data, associated with at least a portion of a brain, received prior to a surgery before occurrence of tissue deformation, in accordance with an embodiment of the disclosure. FIG. 3A is explained in conjunction with elements from FIG. 1 and FIG. 2. With reference to FIG. 3A, there is shown MRI data 302, a brain 304, a cortex structure 304A, a vessel structure 304B, a ventricular structure 304C, a first 3D structure 306 of the brain 304, and a second 3D structure 308 of the brain 304.

In accordance with the exemplary scenario, the MRI data 302 may correspond to the dataset associated with the anatomical portion 112, such as the brain 304, received from the MRI scanner. The MRI data 302 may be captured prior to a surgery. The MRI data 302 may include a plurality of 2D images that represent slice planes taken through a volume of the brain 304, such as slices through head of the human subject 114. The brain 304 may correspond to the anatomical portion 112 of the human subject 114. The cortex structure 304A, the vessels structure 304B, and the ventricular structure 304C may correspond to the plurality of surface structures of the brain 304. In accordance with an embodiment, the cortex structure 304A may correspond to cerebrum cortex and cerebellum cortex. The first 3D structure 306 of the brain 304 may correspond to the 3D structure obtained from the 2D-to-3D mesh geometry processing. The second 3D structure 308 of the brain 304 may correspond to another 3D structure obtained from the 2D-to-3D grid geometry processing.

In accordance with an embodiment, the processor 202 may be configured to receive the MRI data 302 from the MRI scanner. The MRI data 302 may be stored in the memory 204 of the electronic device 102. In accordance with an embodiment, the MRI data 302 may be stored at a central storage location, such as the server 108. In such a case, the processor 202 may receive the MRI data 302 from the server 108, via the communication network 110, by use of the network interface 208.

In accordance with an embodiment, the processor 202 may be configured to process the received MRI data 302 to identify relevant content across the MRI data 302 to perform registration. In accordance with an embodiment, for registration of the MRI data 302, the processor 202 may be configured to align a bone structure of a skull segment of the human subject 114. The processor 202 may be configured to register the received MRI data 302 associated with the brain 304. Based on the registration, the processor 202 may be configured to reconstruct the plurality of surface structures of the brain 304, such as the cortex structure 304A, the vessels structure 304B, and the ventricular structure 304C, as shown in FIG. 3A.

In accordance with an embodiment, the processor 202 may be configured to perform surface segmentation for the reconstructed plurality of surface structures of the brain 304, or at least a portion of the brain 304. The surface segmentation may be performed when the brain 304 is in an unopened state prior to the surgery. In such unopened state, the tissue of the brain 304 may not be deformed.

In accordance with an embodiment, the processor 202 may be configured to create one or more 3D structures, depicted by 306 and 308, of the brain 304, based on the 2D-to-3D geometry processing and the surface segmentation. The first 3D structure 306 of the brain 304 may be an example of the 3D structure of brain 304 obtained from the mesh geometry processing technique. The second 3D structure 308 may be another example of the 3D structure of brain 304 obtained from the 2D-to-3D grid geometry processing technique. The first 3D structure 306 depicts the reconstructed vessels structure 304B and the ventricular structure 304C. The first 3D structure 306 further depicts the cortex structure 304A in a triangular mesh form. The second 3D structure depicts the reconstructed cortex structure 304A, and some of the vessels of the structure 304B, overlaid on the surface of the cortex structure 304A.

The processor 202 may be configured to control display of one or more views of the created 3D structures 306 and 308 of the brain 304, other associated MRI data 302 of the brain 304, and/or the pre-stored physiological data of the subject, such as a patient, on the display 210. The surgeon 116 may plan the surgery to be conducted for the brain 304 based on the displayed one or more views.

Figure 3B:
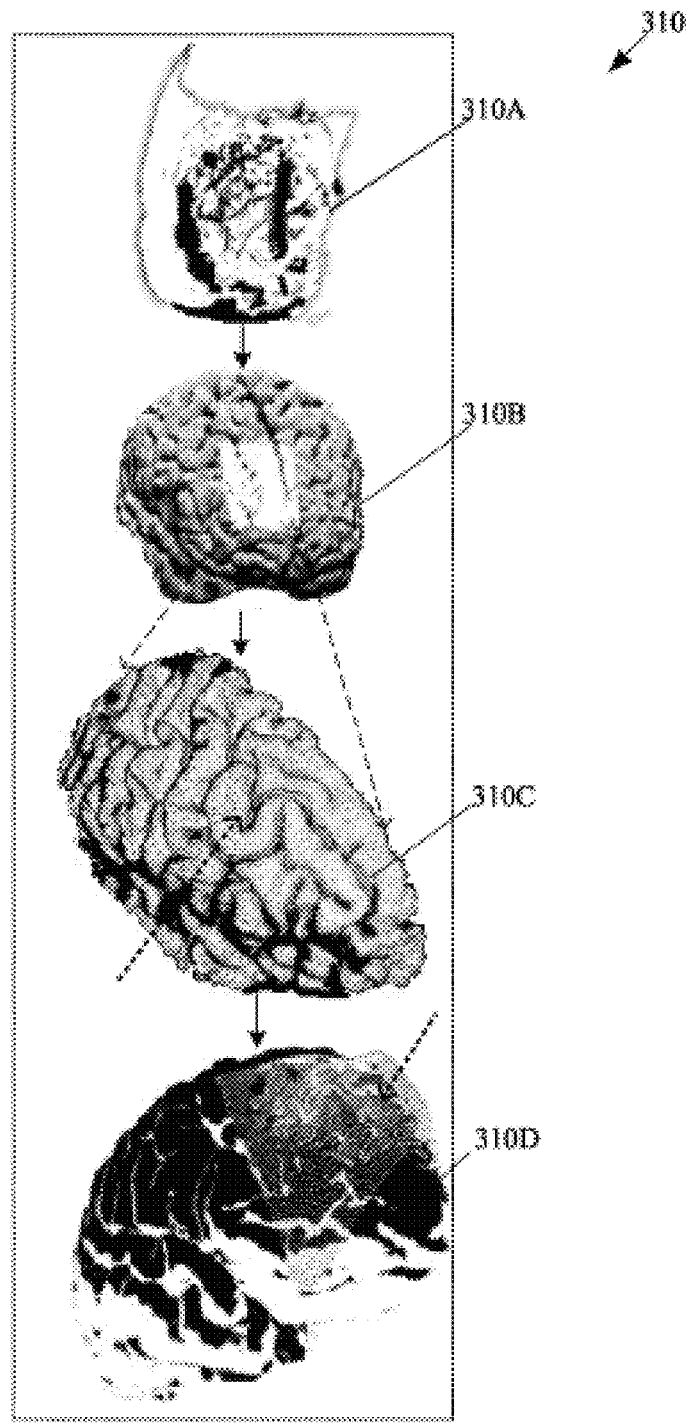

FIG. 3B illustrates 3D surface reconstruction of the brain 304 after deformation based on stereo vision, in the exemplary scenario for implementation of the system and method, in accordance with an embodiment of the disclosure. FIG. 3B is explained in conjunction with elements from FIGS. 1, 2, and 3A. With reference to FIG. 3B, there is shown a schematic view 310 of stereo surface reconstruction of the brain 304 when the brain 304 in an opened state during the surgery. There is further shown stereoscopic data 310A and 3D-structure data 310B for the brain 304. A first enlarged cut-section 310C and a second enlarged cut-section 310D from the 3D-structure data 310B of the brain 304, is further shown in FIG. 3B.

In accordance with an embodiment, the one or more stereo cameras 106 may be used to capture stereoscopic data 310A and generate 3D stereoscopic images or 3D-structure data 310B, for the brain 304 in the intraoperative state. Some of the existing systems and technologies may use intraoperative MRI imaging used to visualize the anatomical structures and presence of deformation. Such intraoperative MRI imaging may be unsafe for the subject due to a risk of exposure to radiation when the tissue of the anatomical portion 112 is exposed during the surgery. Further, a surgical room may not be equipped with necessary MRI scanners and/or the plurality of the medical imaging devices 104. Hence, a patient, such as the human subject 114, may need to be moved to another room for such medical imaging in the intraoperative stage, which further increases the risk to life. Thus, the deployment of the one or more stereo cameras 106 in a surgical room, instead of the bulky MRI scanners, may be relatively safe and easy. Further, there is no risk of radiation exposure to the tissue of the anatomical portion 112 in the intraoperative state from the stereo vision.

The processor 202 may be configured to reconstruct one or more surfaces, such as the cortex and vessels of the brain 304, after tissue deformation, from the 3D-structure data 310B for the brain 304. The first enlarged cut-section 310C of the brain 304 shows the surface reconstruction that corresponds to cortex structure (shown by dotted arrow mark) of the brain 304 (after deformation). The second enlarged cut-section 310D of the brain depicts reconstruction of vessels structure (shown by dotted arrow mark), after the tissue deformation, on the surface of the brain 304 based on stereo vision. In accordance with an embodiment, the processor 202 may be configured to perform a registration of the reconstructed one or more surfaces of the brain 304 (after deformation), to the created 3D structures 306 and 308 of the brain 304 (before deformation), in a 3D coordinate system.

Figure 3C:
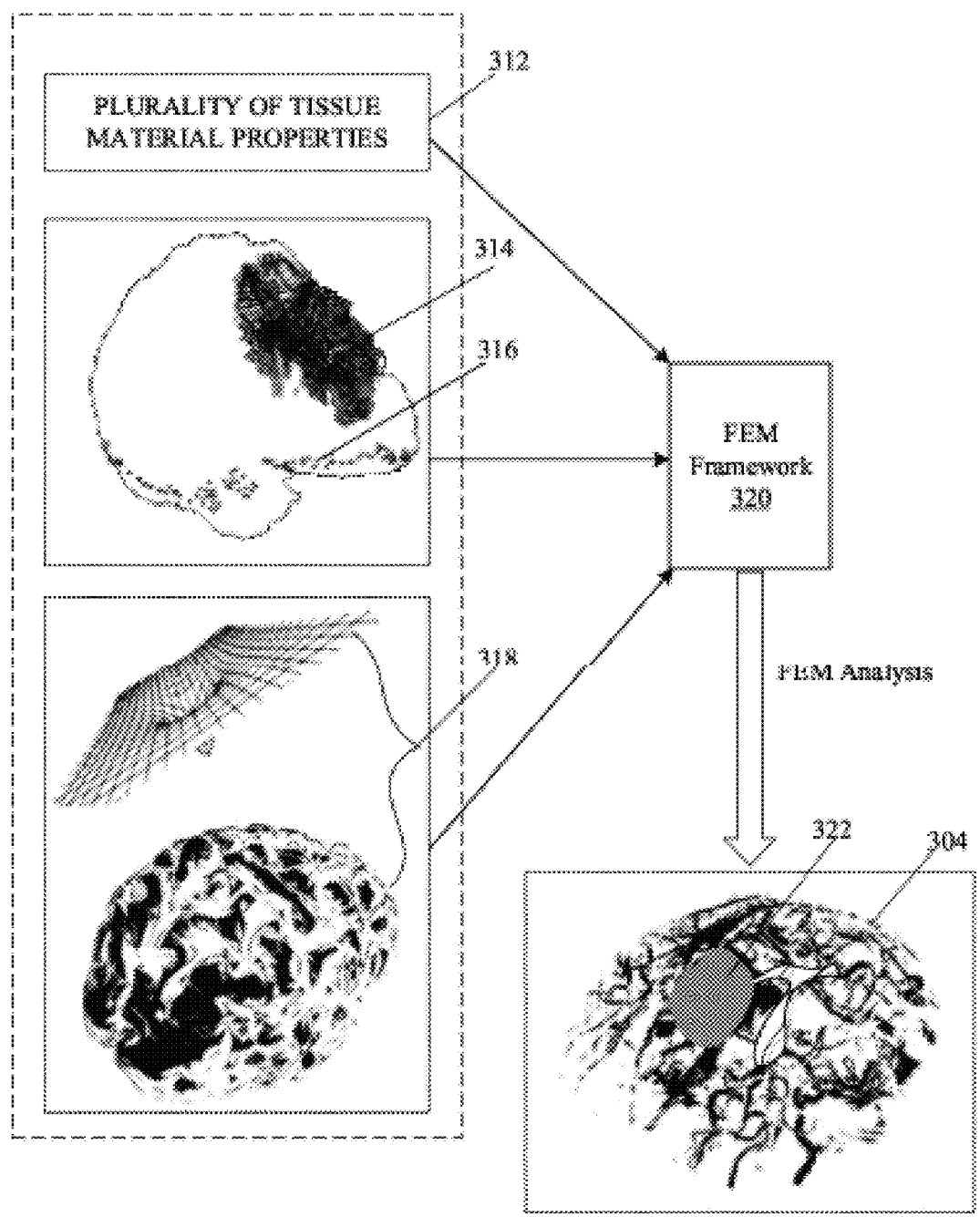

FIG. 3C illustrates surface deformation measurements of the brain 304 by use of the FEM framework in the exemplary scenario for implementation of the system and method, in accordance with an embodiment of the disclosure. FIG. 3C is explained in conjunction with elements from FIGS. 1, 2, 3A, and 3B. With reference to FIG. 3C, there is shown a plurality of tissue material properties 312, a deformation boundary condition 314, a stationary boundary condition 316, surface displacement measurement data 318, an FEM framework 320, and a volume displacement field 322 of the brain 304.

In accordance with an embodiment, the processor 202 may be configured to receive the plurality of tissue material properties 312, such tissue material property of the cortex structure, the vessels structure, the ventricular structure, of the brain 304. In accordance with an embodiment, the processor 202 may be configured to compute the deformation boundary condition 314 and the stationary boundary condition 316 of the brain 304. In accordance with an embodiment, the deformation boundary condition 314 and the stationary boundary condition 316 may be pre-determined for various anatomical portions of subject, such as the brain 304. The processor 202 may receive the deformation boundary condition 314 and the stationary boundary condition 316 of the brain 304.

In accordance with an embodiment, the processor 202 may be configured to determine surface displacement associated with the brain 304 by matching surfaces of brain 304 before and after the deformation. Surface displacement measurement data 318 that corresponds to the determined surface displacement associated with the brain 304 may be stored in the memory 204.

Some of the existing technology may perform point matching to determine displacement instead of matching two surfaces directly, which may be a time-consuming and computationally intensive process. As two corresponding surfaces before and after deformation may be matched directly, the processor 202 may quickly determine the surface displacement of the brain 304. The quick determination of the surface displacement may further expedite other related and subsequent processes, which in turn may be advantageous in provision of quick and timely assistance to the surgeon 116 during the performance of the surgery.

In accordance with an embodiment, the received plurality of tissue material properties 312 of the plurality of surface structures may be fed into the FEM framework 320. Further, the received plurality of boundary conditions, such as the deformation boundary condition 314 and the stationary boundary condition 316, and the surface displacement measurement data 318 may further be fed into the FEM framework 320.

The FEM framework 320 and/or biochemical modeling may be utilized by the processor 202 for the computation of the volume displacement field 322. In accordance with an embodiment, the processor 202 may compute the volume displacement field 322 of the brain 304, based on the received surface displacement measurement data 318, the received plurality of tissue material properties 312, and the received deformation boundary condition 314, and the stationary boundary condition 316.

Figure 3D:
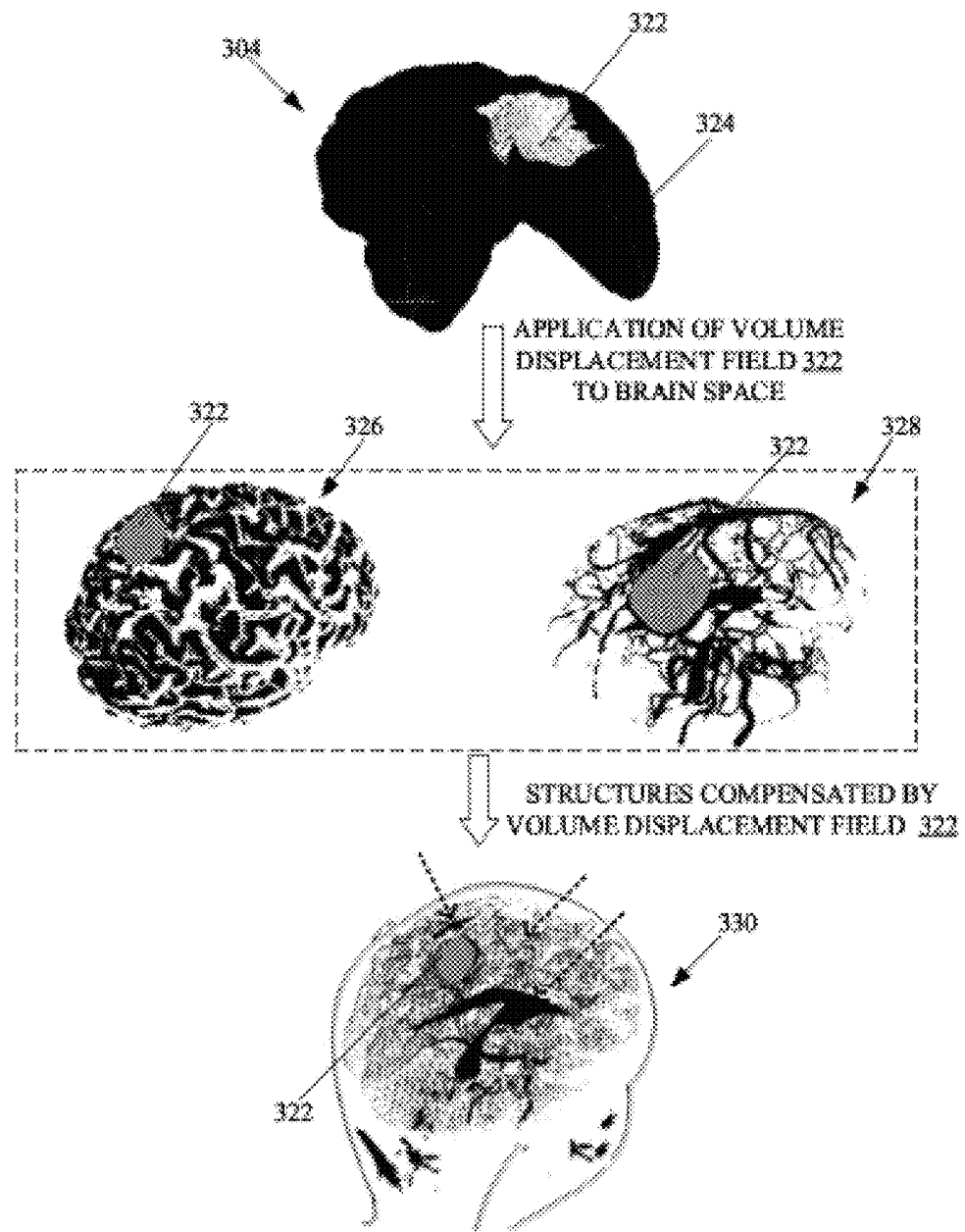

FIG. 3D illustrates deformation compensation in the exemplary scenario for implementation of the system and method, in accordance with an embodiment of the disclosure. FIG. 3D is explained in conjunction with elements from FIGS. 1, 2, 3A, 3B, and 3C. With reference to FIG. 3D, there is shown a cutaway view 324 of the brain 304 with the volume displacement field 322. There is further shown a first view 326 and a second view 328 of the brain 304, which depicts the application of the volume displacement field 322 in the brain space, and an output 3D structure 330 of the brain 304, with the anatomical structures compensated by the volume displacement field 322.

In accordance with an embodiment, the processor 202 may be configured to measure displacement of voxels within the volume of the brain 304 (after the deformation with respect to volume of the brain 304 before the deformation) in the FEM framework 320. The volume of the brain 304 may correspond to the entire tissue content of the brain 304 and not just the surface structures of the brain 304. The measurement of the displacement of voxels may correspond to the propagation of the computed volume displacement field 322.

In accordance with an embodiment, the processor 202 may be configured to apply the computed volume displacement field 322 in the brain space. This may be done for deformation compensation to one or more of the plurality of surface structures of the brain 304. The first view 326 depicts application of the computed volume displacement field 322 in the brain space to compensate the cortex structure 304A of the brain 304. The second view 328 depicts application of the computed volume displacement field 322 in the brain space to compensate other anatomical structures, such as the vessels structure 304B and the ventricular structure 304C, of the brain 304. The processor 202 may be configured to perform a volume interpolation based on the measured displacement of voxels within the volume of the brain 304. The volume interpolation may be a dense interpolation from the computed volume displacement field 322 that may be in a scattered form in the FEM framework 320.

In accordance with an embodiment, the processor 202 may be configured to generate the output 3D structure 330 with anatomical structures, such as the plurality of surface structures (shown by dotted arrow marks). Such plurality of surface structures may be accurately compensated by the volume displacement field 322. The generation of the output 3D structure 330 with the compensated plurality of surface structures may be further based on the volume interpolation.

The generation and subsequent display of the output 3D structure 330 with the compensated plurality of surface structures may occur in real-time or near real-time while the surgeon 116 performs the surgery of the brain 304. In accordance with an embodiment, the output 3D structure 330 and other of the plurality of multi-dimensional graphical views of the brain 304 may be used in various intraoperative applications. For example, the generated output 3D structure 330 may be employed in quantification of tissue deformation which in turn is used to determine the viability of the deformed tissue.

In accordance with an embodiment, the processor 202 may be configured to control display of a plurality of multi-dimensional graphical views of the brain 304 after deformation. The output 3D structure 330 may be one or more of the plurality of multi-dimensional graphical views of the brain 304. The other generated plurality of multi-dimensional graphical views may also include displaced one or more regions-of-interest in the plurality of surface structures of the brain 304 and/or volume displacement within the brain 304. The plurality of multi-dimensional graphical views from one or more perspectives may correspond to a 3D view of the brain 304 that includes the plurality of surface structures. Such a generation and display of the plurality of multi-dimensional graphical views of the brain 304 may provide quick and accurate assistance to the surgeon 116 in presence of the tissue deformation of the brain 304.

In accordance with an embodiment, the plurality of multi-dimensional graphical views may be rendered on the UI that may be displayed on the display 210. The displayed plurality of multi-dimensional graphical views may be interactive and user-controlled, based on input received from the I/O device 206. Such an enhanced visualization of the multi-dimensional graphical views that include the compensated plurality of surface structures of the brain 304 may be utilized for provision of real-time or near real-time assistance in the surgery, such as the image-guided or robot-assisted open cranial surgery of the human subject 114.

Figure 4A:
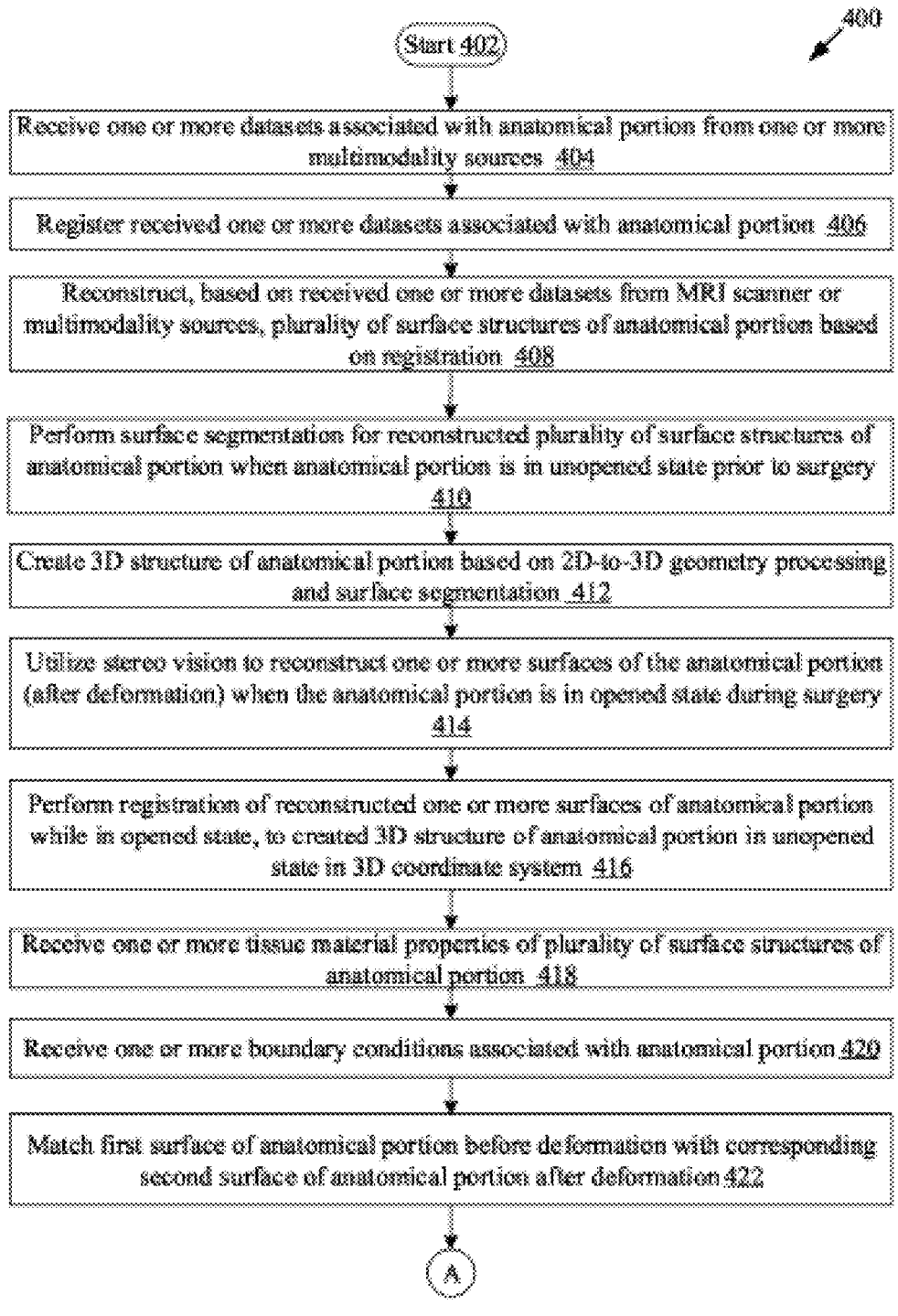
FIGS. 4A and 4B, collectively, illustrate a flow chart for implementation of an exemplary method to provide assistance in a surgery in presence of tissue deformation, in accordance with an embodiment of the disclosure.
Figure 4B:
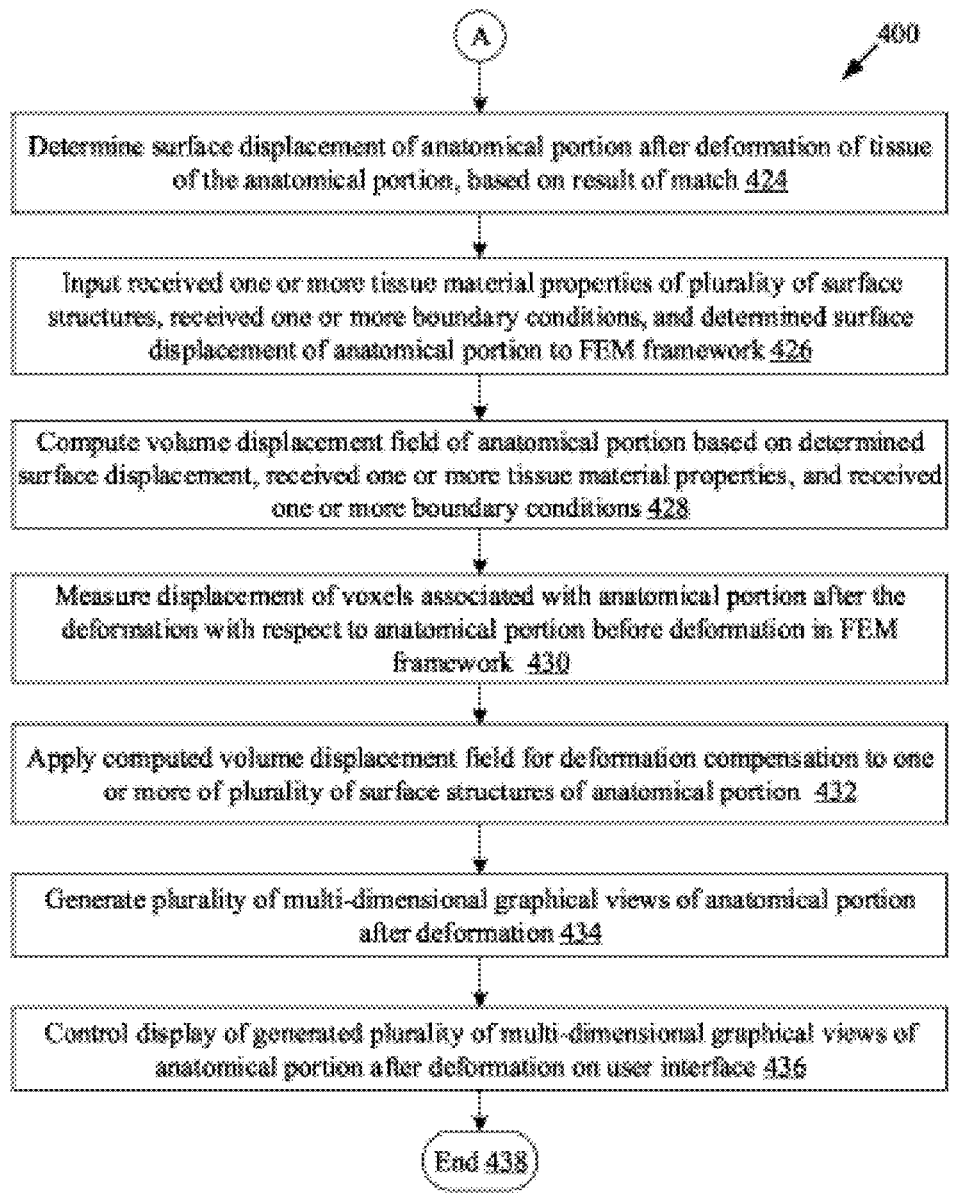

FIGS. 4A and 4B, collectively, illustrate a flowchart for implementation of an exemplary method to provide assistance in a surgery in presence of tissue deformation, in accordance with an embodiment of the disclosure. With reference to FIGS. 4A and 4B, there is shown a flowchart 400. The flowchart 400 is described in conjunction with elements from FIGS. 1, 2, and 3A to 3D. The method, in accordance with the flowchart 400, may be implemented in the electronic device 102. The method starts at step 402 and proceeds to step 404.

At step 404, one or more datasets associated with the anatomical portion 112 may be received from one or more multimodal sources, such as the plurality of medical imaging devices 104. The received one or more datasets may correspond to medical imaging, such as the MRI, performed on the anatomical portion 112 prior to a surgery. An example of the dataset may be the MRI data 302 associated with the brain 304 received from the MRI scanner, as described in FIG. 3A.

At step 406, the received one or more datasets associated with the anatomical portion 112 may be registered. In instances when a plurality of datasets is received from the multimodal sources, the received plurality of datasets may be registered based on identification of overlapped content across the received plurality of datasets.

At step 408, based on the received one or more datasets from the MRI scanner or the multimodal sources, a plurality of surface structures of the anatomical portion 112 may be reconstructed, based on the registration. An example of the reconstructed plurality of surface structures of the anatomical portion 112 may be the cortex structure 304A, the vessels structure 304B, and the ventricular structure 304C of the brain 304, as shown and described in the FIG. 3A.

At step 410, surface segmentation may be performed for the reconstructed plurality of surface structures of the anatomical portion 112. The surface segmentation may be performed by use of the MRI data, such as the MRI data 302, before the deformation of tissue of the anatomical portion 112 when the anatomical portion 112 is in an unopened state prior to a surgery.

At step 412, a 3D structure of the anatomical portion 112 may be created based on a 2D-to-3D geometry processing and the surface segmentation. The 2D-to-3D geometry processing may be a mesh geometry processing or a grid geometry processing. An example of the created 3D structure of the anatomical portion 112 may be the first 3D structure 306 of the brain 304 obtained from the mesh geometry processing technique, and/or the second 3D structure 308 obtained from the 2D-to-3D grid geometry processing technique (FIG. 3A).

At step 414, stereo vision may be utilized to reconstruct one or more surfaces of the anatomical portion 112 (after deformation) when the anatomical portion 112 is in an opened state during the surgery. For example, the one or more stereo cameras 106 may be used to capture stereoscopic data 310A and generate 3D stereoscopic images or 3D-structure data 310B for the brain 304, in the intraoperative state. One or more surfaces, such as cortex and vessels of the brain 304, may be reconstructed after tissue deformation, from the 3D-structure data 310B for the brain 304 (FIG. 3B).

At step 416, a registration of the reconstructed one or more surfaces of the anatomical portion 112 may be performed while in the opened state, to the 3D structure of the anatomical portion 112 in the unopened state in a 3D coordinate system. For example, the reconstructed one or more surfaces of the brain 304 (after deformation), may be registered to the created 3D structures 306 and 308 of the brain 304 (before deformation), in a 3D coordinate system.

At step 418, one or more tissue material properties of the plurality of surface structures of the anatomical portion 112, may be received. An example of the one or more tissue material properties may be the tissue material property of the cortex structure 304A, the vessels structure 304B, and/or the ventricular structure 304C, of the brain 304.

At step 420, one or more boundary conditions associated with the anatomical portion 112, may be further received. An example of the one or more boundary conditions associated with the anatomical portion 112 may be the deformation boundary condition 314 and the stationary boundary condition 316 of the brain 304.

At step 422, a first surface of the anatomical portion 112 before deformation may be matched with a corresponding second surface of the anatomical portion 112 after deformation. The first surface of the anatomical portion 112 may correspond to at least one or more surfaces of the created 3D structure before deformation. The second surface of the anatomical portion 112 may correspond to the reconstructed one or more surfaces of the anatomical portion 112 after deformation.

At step 424, surface displacement of the anatomical portion 112 may be determined after deformation of tissue of the anatomical portion 112, based on a result of the match. An example of the determined surface displacement of the anatomical portion 112 may be the surface displacement measurement data 318 that corresponds to the determined surface displacement associated with the brain 304.

At step 426, the received one or more tissue material properties of the plurality of surface structures, the received one or more boundary conditions, and the determined surface displacement of the anatomical portion 112 may be fed into an FEM framework, such as the FEM framework 320. The FEM framework and/or a biochemical modeling may be employed to analyze the received data.

At step 428, a volume displacement field of the anatomical portion 112 may be computed based on the determined surface displacement, the received one or more tissue material properties, and the received one or more boundary conditions. The electronic device 102 may be configured to utilize the FEM framework for such computation of the volume displacement field of the anatomical portion 112. An example of the computed volume displacement field of the anatomical portion 112 may be the volume displacement field 322 of the brain 304, as shown and described in the FIG. 3C.

At step 430, the displacement of voxels associated with the anatomical portion 112 after the deformation may be measured with respect to the anatomical portion 112 before the deformation in the FEM framework. The displacement of voxels may be measured for the entire tissue content of the anatomical portion 112.

At step 432, the computed volume displacement field may be applied to one or more of the plurality of surface structures of the anatomical portion 112 for deformation compensation. For example, the first view 326 depicts the application of the computed volume displacement field 322 in the brain space to compensate the cortex structure 304A of the brain 304. The second view 328 depicts application of the computed volume displacement field 322 in the brain space to compensate other anatomical structures, such as the vessels structure 304B, and the ventricular structure 304C, of the brain 304 (FIG. 3D). A volume interpolation may be performed based on the measured displacement of voxels within the volume of the brain 304.

At step 434, a plurality of multi-dimensional graphical views of the anatomical portion 112 after the deformation may be generated. The generated plurality of multi-dimensional graphical views may include the displaced one or more regions-of-interest in the plurality of surface structures of the anatomical portion 112, and/or volume displacement within the anatomical portion 112. The volume displacement may represent a change in volume of the anatomical portion 112 and/or the displaced tissue regions due to the deformation. An example of the generated plurality of multi-dimensional graphical views may be the output 3D structure 330 of the brain 304, which may include the compensated plurality of surface structures of the brain 304.

At step 436, display of the generated plurality of multi-dimensional graphical views of the anatomical portion 112 after the deformation on the UI may be controlled, based on user input. The user input may be received by use of the UI rendered on the display 210 of the electronic device 102. The display of the plurality of multi-dimensional graphical views may be changed and updated in response to the received user input, such as an input provided by the surgeon 116. Control passes to end step 438.

In accordance with an embodiment of the disclosure, the system to provide assistance in a surgery in presence of tissue deformation may comprise the electronic device 102 (FIG. 1). The electronic device 102 may comprise one or more circuits, such as the processor 202 (FIG. 2). The processor 202 may be configured to receive one or more tissue material properties of the plurality of surface structures of the anatomical portion 112. The processor 202 may be further configured to receive one or more boundary conditions associated with the anatomical portion 112. The processor 202 may be further configured to determine surface displacement of the anatomical portion 112 by a match of a first surface of the anatomical portion 112 before deformation with a corresponding second surface of the anatomical portion after the deformation. The processor 202 may be further configured to compute the volume displacement field of the anatomical portion 112, based on the determined surface displacement, the received one or more tissue material properties, and the received one or more boundary conditions.

Various embodiments of the disclosure may provide a non-transitory computer readable medium and/or storage medium, and/or a non-transitory machine readable medium and/or storage medium with a machine code and/or a set of instructions stored thereon and executable by a machine and/or a computer to provide assistance in a surgery in the presence of tissue deformation. The set of instructions in the electronic device 102 may cause the machine and/or computer to perform the steps that comprise receipt of one or more tissue material properties of a plurality of surface structures of the anatomical portion 112 (FIG. 1). One or more boundary conditions associated with the anatomical portion 112 may be received. The surface displacement of the anatomical portion 112 may be determined by matching a first surface of the anatomical portion 112 before deformation with a corresponding second surface of the anatomical portion 112 after the deformation. The volume displacement field of the anatomical portion 112 may be computed based on the determined surface displacement, the received one or more tissue material properties, and the received one or more boundary conditions.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system that has an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departure from its scope. Therefore, it is intended that the present disclosure not be limited to the particular embodiment disclosed, but that the present disclosure will include all embodiments that falls within the scope of the appended claims.

What is claimed is:

1. A system for surgery assistance, said system comprising:
one or more circuits in an electronic device configured to:
receive information related to at least one tissue material property of a plurality of surface structures of an anatomical portion;
receive at least one boundary condition associated with a propensity of deformation of said plurality of surface structures of said anatomical portion;
match a first surface of said anatomical portion before said deformation of said plurality of surface structures of said anatomical portion directly with a corresponding second surface of said anatomical portion after said deformation;
determine surface displacement of said anatomical portion based on said match of said first surface with said corresponding second surface;
compute volume displacement field of said anatomical portion based on said determined surface displacement, said received information, and said received at least one boundary condition; and
apply said computed volume displacement to at least one of said plurality of surface structures for compensation of said deformation in a graphical view of said anatomical portion.

2. The system according to claim 1, wherein said plurality of surface structures corresponds to heterogeneous anatomical surface structures.

3. The system according to claim 1, wherein
said anatomical portion corresponds to at least a portion of a brain, and
said plurality of surface structures corresponds to at least two of cortex, vessels, ventricles, or a tumor structure in said anatomical portion of a subject.

4. The system according to claim 1, wherein said received at least one boundary condition includes at least one of a displaced boundary condition or a stationary boundary condition.

5. The system according to claim 1, wherein
said one or more circuits are further configured to reconstruct said plurality of surface structures of said anatomical portion based on registration of a dataset,
said dataset is associated with said anatomical portion,
said dataset is received from at least one of a magnetic resonance imaging (MRI) scanner or multimodality sources including said MRI scanner, and
said dataset is registered based on identification of overlapped content of said dataset.

6. The system according to claim 1, wherein
said one or more circuits are further configured to segment surfaces for said plurality of surface structures by surface segmentation, and
said surface segmentation is based on MRI data before said deformation and said anatomical portion that is in an unopened state prior to surgery.

7. The system according to claim 6, wherein
said one or more circuits are further configured to create a three-dimensional (3D) structure of said anatomical portion based on a two-dimensional (2D) to 3D geometry process and said surface segmentation, said created 3D structure comprises said plurality of surface structures, and said plurality of surface structures corresponds to said first surface.

8. The system according to claim 7, wherein said one or more circuits are further configured to reconstruct at least one surface of said anatomical portion after said deformation, said at least one surface is reconstructed based on stereo vision for said determination of said surface displacement, and said anatomical portion that is in an opened state during said surgery, and said reconstructed at least one surface of said anatomical portion after said deformation corresponds to said corresponding second surface.

9. The system according to claim 8, wherein said one or more circuits are further configured to register said reconstructed at least one surface of said anatomical portion in said opened state to said 3D structure of said anatomical portion in said unopened state, in a 3D coordinate system, and said reconstructed at least one surface is registered based on an alignment of bone structure of a skull of a subject, and said anatomical portion that is at least a portion of a brain of said subject.

10. The system according to claim 1, wherein said one or more circuits are further configured to measure displacement of voxels associated with said anatomical portion after said deformation with respect to said anatomical portion before said deformation, said displacement of voxels is measured in a finite element method (FEM) framework, said displacement of voxels is measured within volume of said anatomical portion, said volume of said anatomical portion corresponds to entire tissue content of said anatomical portion, said displacement of voxels is measured based on said determined surface displacement, and a measurement of said displacement of voxels corresponds to said computation of said volume displacement field.

11. The system according to claim 1, wherein said one or more circuits are further configured to generate, to assist during a surgery, a plurality of multi-dimensional graphical views of said anatomical portion after said deformation, said plurality of multi-dimensional graphical views are generated based on said anatomical portion that is deformed in an opened state, said generated plurality of multi-dimensional graphical views comprises at least one of at least one displaced region-of-interest in said plurality of surface structures of said anatomical portion or volume displacement within said anatomical portion, and said volume displacement represents a change in volume after said deformation.

12. The system according to claim 11, wherein said plurality of multi-dimensional graphical views corresponds to a plurality of three dimensional views of said anatomical portion, and said plurality of three dimensional views includes said plurality of surface structures from at least one perspective.

13. A method for surgery assistance, said method comprising:

receiving, by one or more circuits in an electronic device, information related to at least one tissue material property of a plurality of surface structures of an anatomical portion;

receiving, by said one or more circuits, at least one boundary condition associated with a propensity of deformation of said plurality of surface structures of said anatomical portion;

matching, by said one or more circuits, a first surface of said anatomical portion before said deformation of said plurality of surface structures of said anatomical portion directly with a corresponding second surface of said anatomical portion after said deformation;

determining, by said one or more circuits, surface displacement of said anatomical portion based on said matching of said first surface with said corresponding second surface;

computing, by said one or more circuits, volume displacement field of said anatomical portion based on said determined surface displacement, said received information, and said received at least one boundary condition; and applying, by said one or more circuits, said computed volume displacement field to at least one of said plurality of surface structures for compensation of said deformation in a graphical view of said anatomical portion.

14. The method according to claim 13, wherein said anatomical portion corresponds to a portion of a brain, and said plurality of surface structures corresponds to at least two of cortex, vessels, ventricles, or tumor structure in said anatomical portion of a subject.

15. The method according to claim 13, wherein said received at least one boundary condition includes at least one of a displaced boundary condition or a stationary boundary condition.

16. The method according to claim 13, further comprising reconstructing, by said one or more circuits, said plurality of surface structures of said anatomical portion based on registration of a dataset, wherein said dataset is associated with said anatomical portion, said dataset is received from at least one of a magnetic resonance imaging (MRI) scanner or multimodality sources including said MRI scanner, and said dataset is registered based on identification of overlapped content of said dataset.

17. The method according to claim 13, further comprising segmenting, by said one or more circuits, surfaces for said plurality of surface structures based on surface segmentation, wherein said surface segmentation is based on MRI data before said deformation and said anatomical portion that is in an unopened state prior to surgery.

18. The method according to claim 17, further comprising creating, by said one or more circuits, a three-dimensional (3D) structure of said anatomical portion based on a two-dimensional (2D) to 3D geometry processing and said surface segmentation, wherein said created 3D structure comprises said plurality of surface structures, and said plurality of surface structures corresponds to said first surface.

19. The method according to claim 18, further comprising reconstructing, by said one or more circuits, at least one surface of said anatomical portion after said deformation, wherein said reconstructed at least one surface is based on stereo vision for said determination of said surface displacement, and said anatomical portion that is in an opened state during said surgery, and said reconstructed at least one surface of said anatomical portion after said deformation corresponds to said corresponding second surface.

20. The method according to claim 19, further comprising, registering, by said one or more circuits, said reconstructed at least one surface of said anatomical portion in said opened state to said 3D structure of said anatomical portion in said unopened state, in a 3D coordinate system, and wherein said reconstructed at least one surface is registered based on an alignment of bone structure of a skull of a subject, and said anatomical portion that is at least a portion of a brain of said subject.

21. The method according to claim 13, further comprises measuring, by said one or more circuits, displacement of voxels associated with said anatomical portion after said deformation with respect to said anatomical portion before said deformation, wherein said displacement of voxels is measured in a finite element method (FEM) framework, said displacement of voxels is measured within volume of said anatomical portion, said volume of said anatomical portion corresponds to entire tissue content of said anatomical portion, said displacement of voxels is measured based on said determined surface displacement, and said measurement of said displacement of voxels corresponds to said computation of said volume displacement field.

22. The method according to claim 13, further comprising generating, by said one or more circuits to assist during a surgery, a plurality of multi-dimensional graphical views of said anatomical portion after said deformation, wherein said plurality of multi-dimensional graphical views are generated based on said anatomical portion that is deformed in an opened state, said generated plurality of multi-dimensional graphical views comprises at least one of at least one displaced region in said plurality of surface structures of said anatomical portion or volume displacement within said anatomical portion, and said volume displacement represents a change in volume after said deformation.

23. The method according to claim 22, wherein said plurality of multi-dimensional graphical views corresponds to a three dimensional view of said anatomical portion, and said three dimensional view includes said plurality of surface structures from at least one perspective.

* * * * *